(12) United States Patent
Latterell et al.

(10) Patent No.: US 6,712,776 B2
(45) Date of Patent: Mar. 30, 2004

(54) ENHANCED INTERSTITIAL FLUID COLLECTION

(75) Inventors: Scott T. Latterell, Minneapolis, MN (US); Paul D. Brinda, Robbinsdale, MN (US); Michael E. Hilgers, Roseville, MN (US); Michael J. Shoup, Maple Grove, MN (US); Thomas B. Hoegh, Minneapolis, MN (US); Brian J. Erickson, Woodbury, MN (US)

(73) Assignee: Integ, Inc., St. Paul, MN (US)

( * ) Notice: Subject to any disclaimer, the term of this patent is extended or adjusted under 35 U.S.C. 154(b) by 120 days.

(21) Appl. No.: 09/812,150

(22) Filed: Mar. 19, 2001

(65) Prior Publication Data

US 2001/0011157 A1 Aug. 2, 2001

Related U.S. Application Data

(63) Continuation of application No. 09/262,146, filed on Mar. 3, 1999, now Pat. No. 6,203,504, which is a continuation of application No. 08/525,942, filed on Sep. 8, 1995, now Pat. No. 5,879,367.

(51) Int. Cl.$^7$ .............................. A61B 5/00; A61B 17/14
(52) U.S. Cl. ...................... 600/576; 600/583; 606/182
(58) Field of Search ................................ 600/573–584; 604/317–326; 606/180, 181

(56) References Cited

U.S. PATENT DOCUMENTS

| | | | |
|---|---|---|---|
| 3,208,452 A | 9/1965 | Stern | |
| 3,338,239 A | 8/1967 | Mausteller | |
| 4,517,978 A | 5/1985 | Levin | |
| 4,622,974 A | 11/1986 | Coleman et al. | |
| 4,637,403 A | 1/1987 | Garcia et al. | |
| 4,648,408 A | 3/1987 | Hutcheson et al. | |
| 4,873,993 A | 10/1989 | Meserol et al. | |
| 4,883,068 A | 11/1989 | Dechow | |
| 4,953,552 A | 9/1990 | DeMarzo | |
| 4,954,318 A | 9/1990 | Yafuso et al. | |
| 4,960,467 A | 10/1990 | Peck | |

(List continued on next page.)

FOREIGN PATENT DOCUMENTS

| | | |
|---|---|---|
| DE | 3708031 | 11/1987 |
| EP | 0 212 906 A2 | 4/1986 |
| EP | 0 199 484 A2 | 7/1986 |
| EP | 0 250 257 A1 | 6/1987 |
| EP | 0160768 B1 | 5/1989 |
| EP | 0 453 283 A1 | 10/1991 |
| EP | 0 582 226 A1 | 7/1993 |
| EP | 555554 | 11/1997 |
| GB | 2033575 A | 5/1980 |
| WO | WO 85/04089 | 9/1985 |
| WO | WO 88/00812 | 2/1988 |
| WO | WO 91/18548 | 12/1991 |
| WO | WO 9300043 | 1/1993 |
| WO | WO 95/10223 | 4/1995 |

OTHER PUBLICATIONS

Brace RA et al., "Reevaluation of the Needle Method of Measuring Interstitial Fluid Pressure," Am J. Physiol (United States) Sep. 1975, 229 (3) p603–7.

(List continued on next page.)

*Primary Examiner*—Max F. Hindenburg
*Assistant Examiner*—David J. McCrosky
(74) *Attorney, Agent, or Firm*—Carol M. LaSalle; Bozicevic, Field & Francis, LLP

(57) ABSTRACT

A sampling apparatus for interstitial fluid includes a pressure ring surrounding a collection needle. The pressure ring and needle are movable relative to one another for the ring to first engage a patient's skin surface prior to insertion of the needle.

13 Claims, 17 Drawing Sheets

U.S. PATENT DOCUMENTS

| | | |
|---|---|---|
| 4,981,779 A | 1/1991 | Wagner |
| 5,002,054 A | 3/1991 | Ash et al. |
| 5,014,718 A | 5/1991 | Mitchen |
| 5,026,388 A | 6/1991 | Ingalz |
| 5,029,583 A | 7/1991 | Meserol et al. |
| 5,035,704 A | 7/1991 | Lambert et al. |
| 5,054,499 A | 10/1991 | Swierczek |
| 5,066,859 A | 11/1991 | Karkar et al. |
| 5,070,886 A | 12/1991 | Mitchen et al. |
| 5,079,421 A | 1/1992 | Knudson et al. |
| 5,115,133 A | 5/1992 | Knudson |
| 5,146,091 A | 9/1992 | Knudson |
| 5,179,951 A | 1/1993 | Knudson |
| 5,201,324 A | 4/1993 | Swierczek |
| 5,231,993 A | 8/1993 | Haber et al. |
| 5,320,607 A | 6/1994 | Ishibashi |
| 5,368,047 A | 11/1994 | Suzuki et al. |
| 5,437,841 A | 8/1995 | Balmer |
| 5,458,140 A | 10/1995 | Eppstein et al. |
| 5,470,757 A | 11/1995 | Gagnon et al. |
| 5,582,184 A | 12/1996 | Erickson et al. |
| 5,682,233 A | 10/1997 | Brinda |
| 5,746,217 A | 5/1998 | Erickson et al. |
| 5,820,570 A | 10/1998 | Erickson et al. |
| 5,879,310 A | 3/1999 | Sopp et al. |
| 5,879,367 A | 3/1999 | Latterell et al. |

OTHER PUBLICATIONS

Gilanyi M. et al., "Ion Concentrations in Subcutaneous Interdtitial Fluid: Measured Versus Expected Values," Am J. Physiol (United States) Sep. 1998, 255 (3 Pt 2) pF513–9.

Petersen LJ et al., "Microdialysis of the Interstitial Water Space in Human Skin In Vivo: Quantative Measurement of Cutaneous Glucose Concentrations," J. Invest Dermatol (United States) Sep. 1992, 99 (3).

Turner APF et al., "Diabetes Mellitus: Biosensors for Reach and Management," Biosensors 1 (1985): 85–115.

Wolfson, Jr. SK et al., "Glucose Concentration at Possible Sensor Tissue Implant Sites," Diabetes Care 5, No. 3 (1982): 162.

"Blood Glucose Measurement by Multiple Attenuated Total Reflection and Infared Absorption Spectroscopy," I.E.E.E. Transactions on Biomedical Engineering, vol. 37, No. 5, May 1990.

"New Non–Invasive Transcutaneous Approach to Blood Glucose Monitoring: Successful Glucose Monitoring on Human 75 g OGTT with Novel Sampling Chamber," I.E.E.E. Transactions on Biomedical Engineering, vol. 38 No 8 Aug. 1991.

"Use of Capillary Filtrate Collector for Monitoring Glucose in Diabetics," vol. XXXIII, Transactions in American Society, Artif. Intern. Organs, 1987.

Korthius et al., "Method for Sampling Intersitial Fluid" from book entitled Microcirculatory Technology, edited by D. H. Baker et al., Academic Press, Chapter 21, 1986.

"Suction Blister Device for Separation of Viable Epidermis from Dermis," vol. 50, No. 2, Journal of Investigative Dermatology, 1968.

"Subcutaneous Capillary Filtrate Collector of Measurement of Blood Glucose," ASAIO Journal, 1992, vol. 38 pp. M416–M420.

"Toward Coninuous Glucose Monitoring: In Vivo Evaluation of Miniturized Glucose Sensor Implanted for Several Days from Rat Subcutaneous Tissue" (Diabetologia Glen, 1992) 35:224–230.

Ginsberg, B., "An Overview of Minimally Invasive Technologies", Clinical Chemistry, vol. 38, No. 9, pp. 1596–1600 (1992).

"Glucose Sensors" and "Like An Injection" sections on p. 26 of Diabetes Forecast, May, 1993.

N. DuPuy et al., "Quantative Analysis of Aqueous Solutions by FTIR Spectroscopy of Dry Extract", SPIE, vol. 1575, 8th International Conference on Fourier Transform Spectroscopy (1991), pp. 501–502.

Ash, Sr., et al., *ASAIO J* (United States), Jul.–Sep. 1993, 39 (3) pM699–705.

Kayashima, S., et al., *Am J. Physiol* (United States), Nov. 1992, 263 (5Pt 2) pH1623–7.

Wiig, H., *Crit Rev Biomed Eng* (United States), 1990, 18 (1) p27–54.

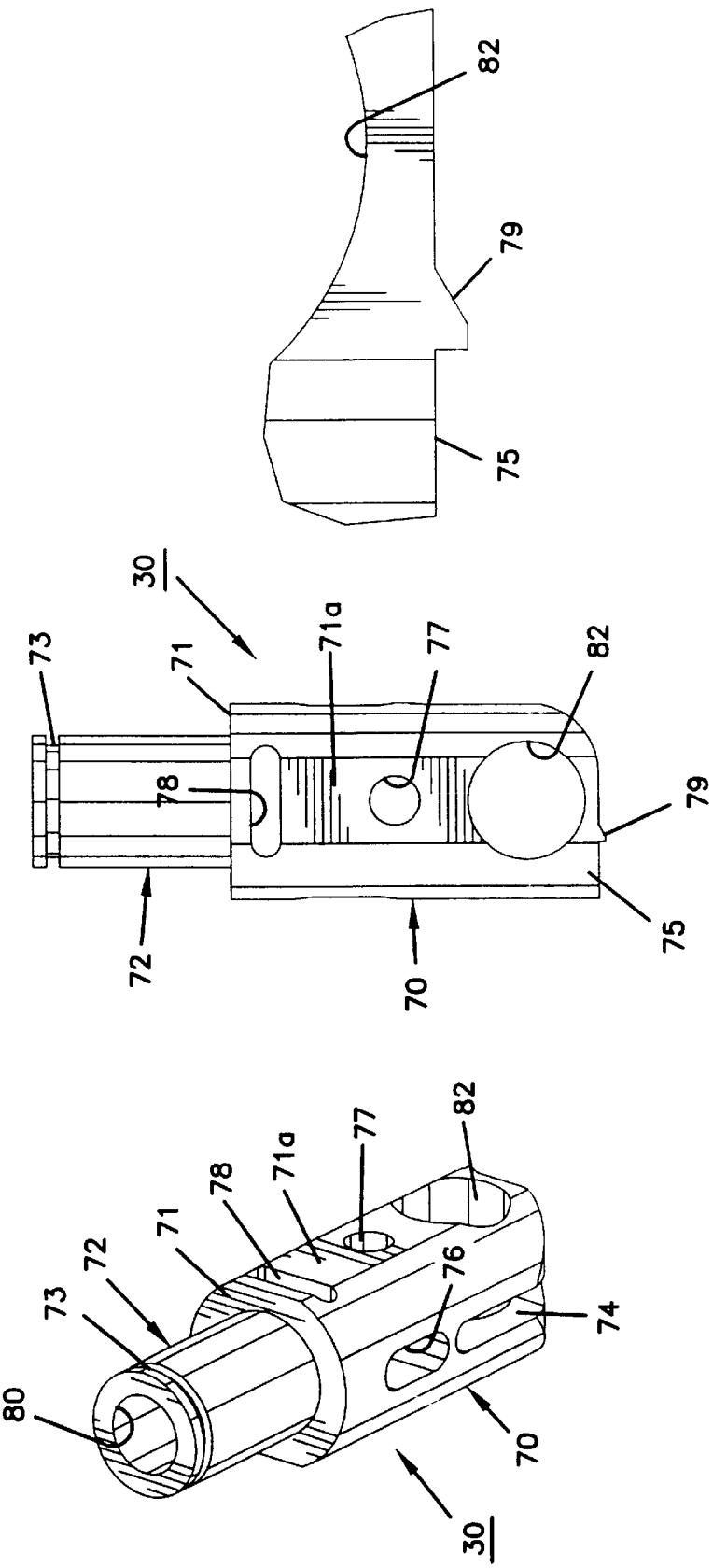

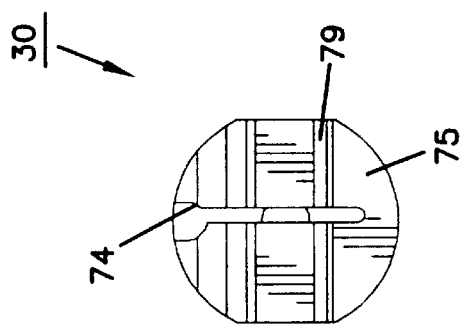
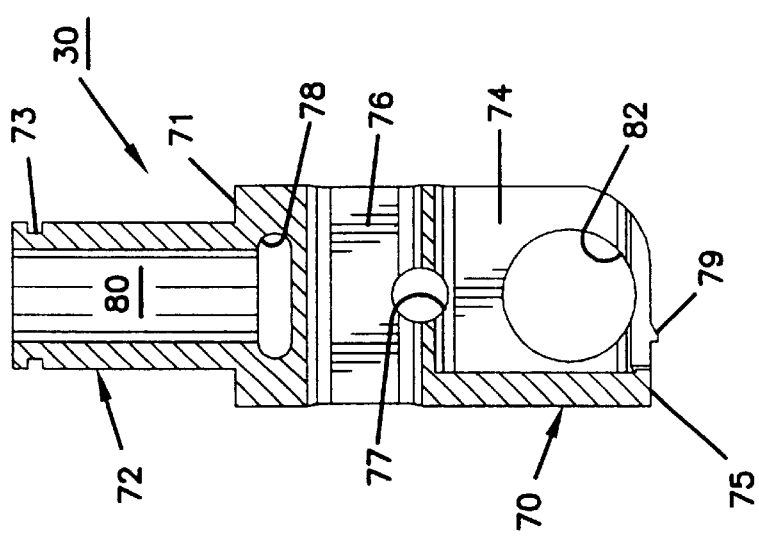
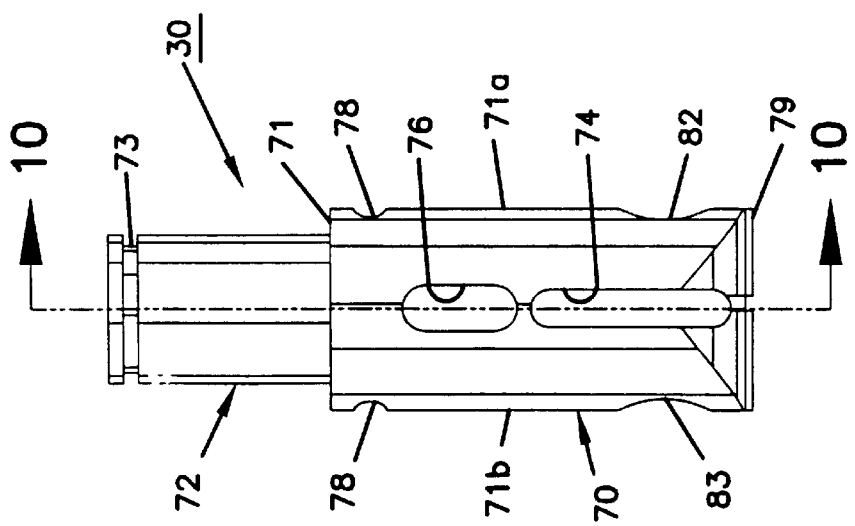

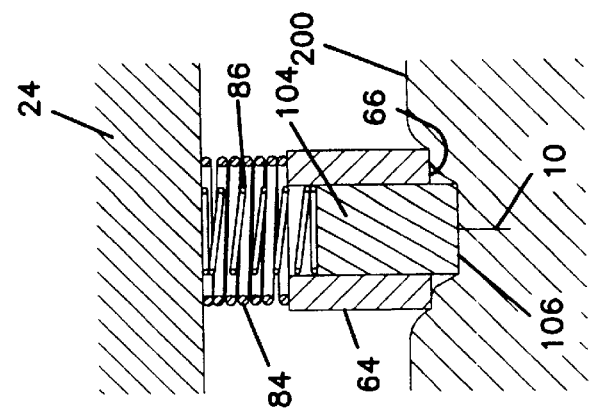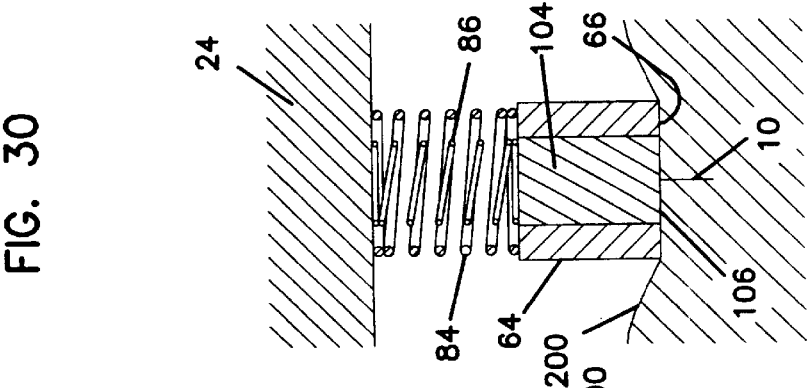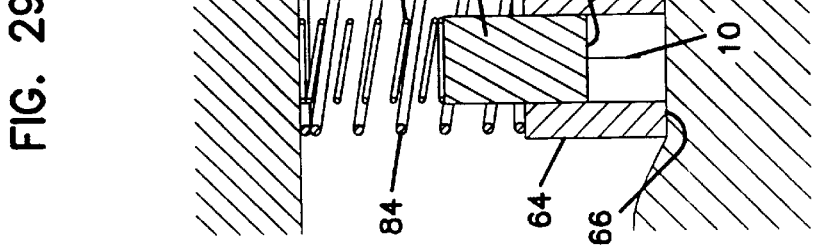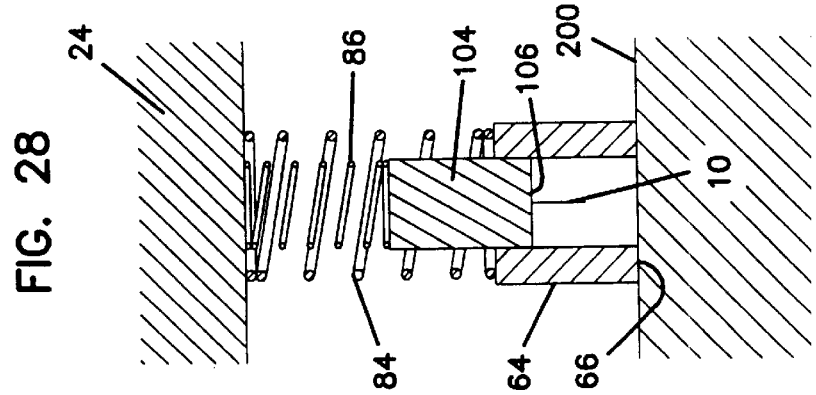

ENHANCED INTERSTITIAL FLUID COLLECTION

I. CROSS-REFERENCE TO RELATED APPLICATION

The present application is a continuation of U.S. patent application Ser. No. 09/262,146, filed on Mar. 3, 1999, now U.S. Pat. No. 6,203,504, issued March 20, 2001, which is a continuation of U.S. patent application Ser. No. 08/525,942, filed Sep. 8, 1995, now U.S. Pat. No. 5,879,367, issued Mar. 9, 1999.

II. BACKGROUND OF THE INVENTION

1. Field of the Invention

This invention pertains to an apparatus for testing body fluid constituents. More particularly, this invention pertains to an apparatus with enhanced interstitial fluid collection.

2. Description of the Prior Art

In the prior art, there are numerous examples of apparatus for testing and determining the level of constituents in human blood. A great deal of attention has been directed to the development of techniques and apparatus for measuring blood glucose.

As noted in commonly assigned and co-pending U.S. patent application Ser. Nos. 08/321,305 and 08/136,304 (corresponding to PCT International Publication No. WO95/10223 published Apr. 20, 1995 on International Application No. PCT/US94/11580 and incorporated herein by reference), the determination of the level of a constituent of blood can be achieved by measuring the level of that constituent in other body fluids such as interstitial fluid. The aforementioned patent applications and international publication disclose a method and apparatus for a minimally invasive technique for collecting a sample of interstitial fluid through use of an extremely small needle which penetrates into the dermal layer of the skin in order to collect a low blood or blood-free sample of interstitial fluid. The collected interstitial fluid can then be analyzed for a determination of the level of constituents within the fluid. For example, the collected interstitial fluid can be analyzed for an amount of glucose with the determined amount being representative of the amount of glucose contained within the patient's blood.

The aforementioned applications and international publication disclose the use of a ring (item 60 in FIG. 6 of the application) which surrounds the needle to create a pressure area on the patient's skin. It is believed this leads to increase the amount of interstitial fluid being collected.

In the collection of interstitial fluid, it is desirable to increase the speed at which a sample is collected. In the absence of mechanical or other assistance, the rate at which interstitial fluid is collected through a small diameter tube or needle is very slow. Preferably, patients utilizing such equipment for home use, will be provided with a system which collects interstitial fluid at a rapid pace to ensure that a patient does not remove the needle too early in its application. Also, it is important to provide for techniques to increase a volume of interstitial fluid being collected through a needle.

When collecting any body fluid through use of a needle, it is important that the needle be a disposable item in order to prevent re-use of the needle. Such re-use can result in the transmission of disease. Where the apparatus is to be used in a patient's home by the patient, the apparatus should be simple to use and with the needle incorporated in a disposable item. Since the needle is incorporated in a disposable item, it is important that the disposable item be amenable to low-cost manufacture. Also, in order to test the interstitial fluid, the interstitial fluid collection mechanism must be coupled with an analytic mechanism for analyzing the collected fluid. Where such a device is to be used in home by low-skilled patients, it is important that the sampler and the analytic portion of the device be mutually configured to ensure that the sampler is coupled to the apparatus in a repeatable and reliable manner to minimize errors resulting from use of the apparatus by untrained patients.

III. SUMMARY OF THE INVENTION

According to a preferred embodiment of the present invention, a sampler for collecting interstitial fluid from a skin layer is disclosed. The sampler includes a sampling needle having an axis and terminating at a distal end. A pressure ring surrounds the needle in spaced relation to the needle. The needle and the pressure ring are movable relative to one another along a path of travel which is generally parallel to the axis of the needle. The needle and ring are movable relative to one another between an extended position and a retracted position. In the extended position, the distal end of the needle extends beyond the ring. In the retracted position, the distal end of the needle is recessed behind the ring. A spring is provided for biasing the needle and the ring to the retracted position.

IV. BRIEF DESCRIPTION OF THE DRAWINGS

FIG. 7 is a perspective view of an optics housing for use in the apparatus of FIG. 1;

FIG. 8 is a side elevation view of the housing of FIG. 7;

FIG. 8A is an enlarged view of a bottom portion of the view of FIG. 8;

FIG. 9 is a side elevation view of the housing of FIG. 7 rotated 90° from the view of FIG. 8;

FIG. 10 is a view taken along line 10—10 of FIG. 9;

FIG. 11 is a bottom plan view of the housing of FIG. 7;

FIG. 28 is a schematic representation showing the apparatus of FIG. 1 placed against a patient's skin;

FIG. 29 is the view of FIG. 28 showing initial forcing of the apparatus against the patient's skin;

FIG. 30 is the view of FIG. 28 showing urging of the apparatus against the patient's skin with penetration of a needle into the patient's skin layer and with a piston aligned with a pressure ring; and FIG. 31 is the view of FIG. 28 with the piston protruding beyond the pressure ring.

V. DESCRIPTION OF THE PREFERRED EMBODIMENT

Figure 1:
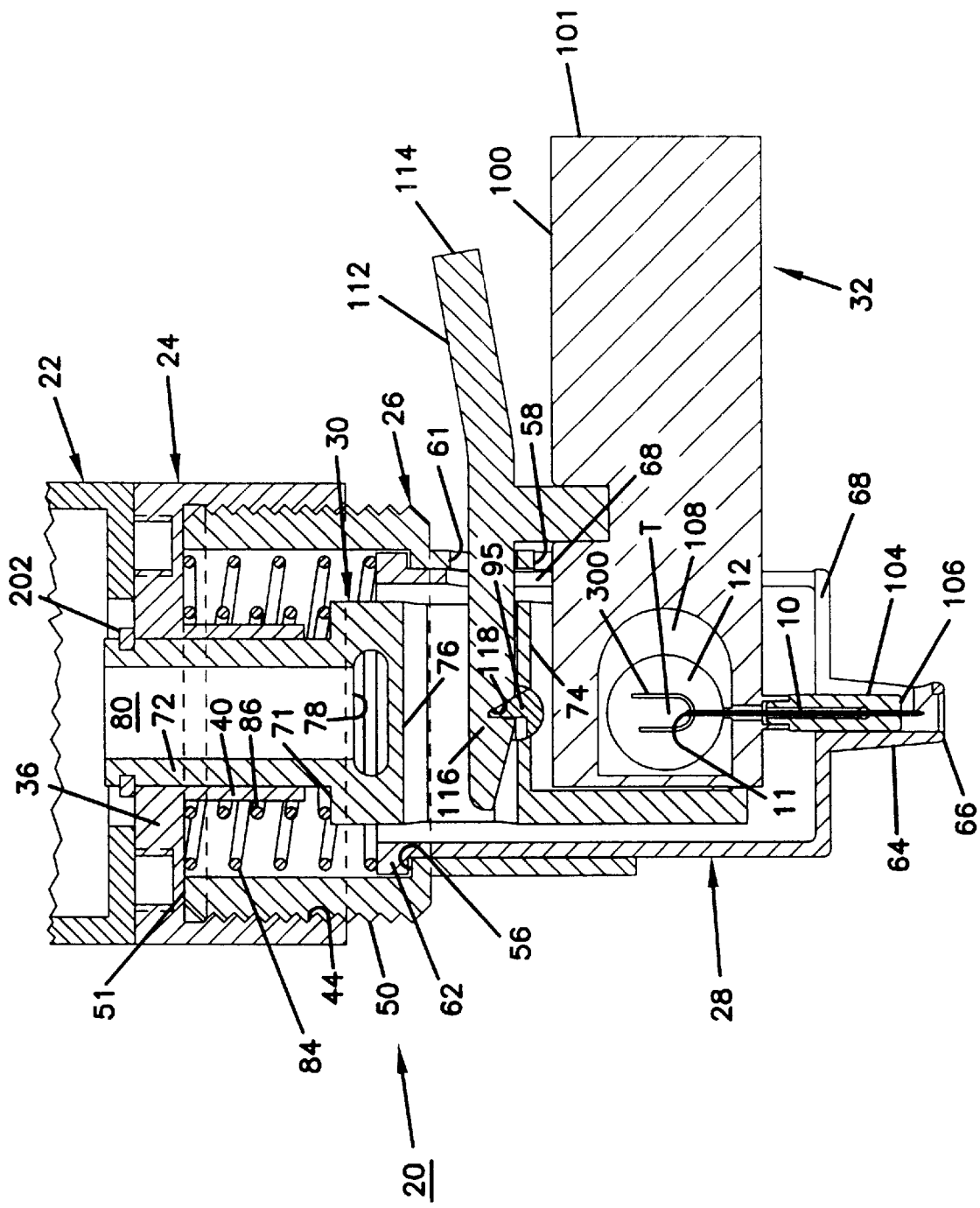
FIG. 1 is a cross-sectional elevation view of an interstitial fluid apparatus showing a sampler contained within the apparatus in a retracted position.

With reference now to the various drawing figures in which identical elements are numbered identically throughout, a description of the preferred embodiment of the present invention will be shown. While the invention will be described with reference to an apparatus for collecting interstitial fluid to test for glucose within the interstitial fluid, it will be appreciated that the apparatus can be used for testing any body constituent which may be contained within interstitial fluid.

In a preferred embodiment, the apparatus is disclosed with reference to use of a penetrating needle and an absorbing membrane such as that shown and described in U.S. patent application Ser. Nos. 08/321,305 and 08/136,304 (and corresponding PCT International Publication No. WP 95/10223, dated Apr. 20, 1995 on International Application No. PCT/US94/11580, incorporated herein by reference). With reference to FIGS. 16–20 of that application (showing a representative embodiment of the invention shown in that application), a needle 214' is surrounded and maintained in fixed relative position by a ring 202'. The ring is placed against a patient's skin in order to define a pressurized area on the patient's skin as the needle 214' penetrates into the skin. The needle is sized to be about 28 to 32 gauge (i.e., 0.36 mm outside diameter to 0.23 mm outside diameter) with an anticipated preferred size of about 30 gauge. The needle is made as small as possible to provide a minimally intrusive and painless insertion into the skin. The needle is sized to penetrate into the dermis for a variety of reasons as best disclosed in the aforementioned application including low pain and the collection of low blood interstitial fluid for subsequent testing. An absorbent membrane 210' is placed in fluid flow communication with the needle 214' such that interstitial fluid which flows through the needle 214' is deposited on the membrane 210' as a spot available for subsequent testing with light (visible or non-visible spectrum). The amount of absorption of various wavelengths of the light indicating the concentration of constituents for testing such as glucose or the like.

The present invention pertains to a testing apparatus which includes a needle 10 disposed in fluid flow communication with an absorbent membrane 12 both in accordance with the teachings of the aforementioned PCT International Publication No. WO95/10223.

The present invention is directed to an apparatus 20 (FIGS. 1–6) for collecting and testing interstitial fluid. The apparatus 20 includes a main housing 22 (shown in FIGS. 1 and 2 only) coupled to a base 24. The apparatus 20 further includes a collar 26 secured to the base 24. A shell 28 is contained within the collar 26. An optics housing 30 is contained within the shell 28. Finally, a sampler 32 is provided to be received within the optics housing 30. Each of base 24, collar 26, shell 28, optics housing 30 and sampler 32 will be separately described.

Figure 2:
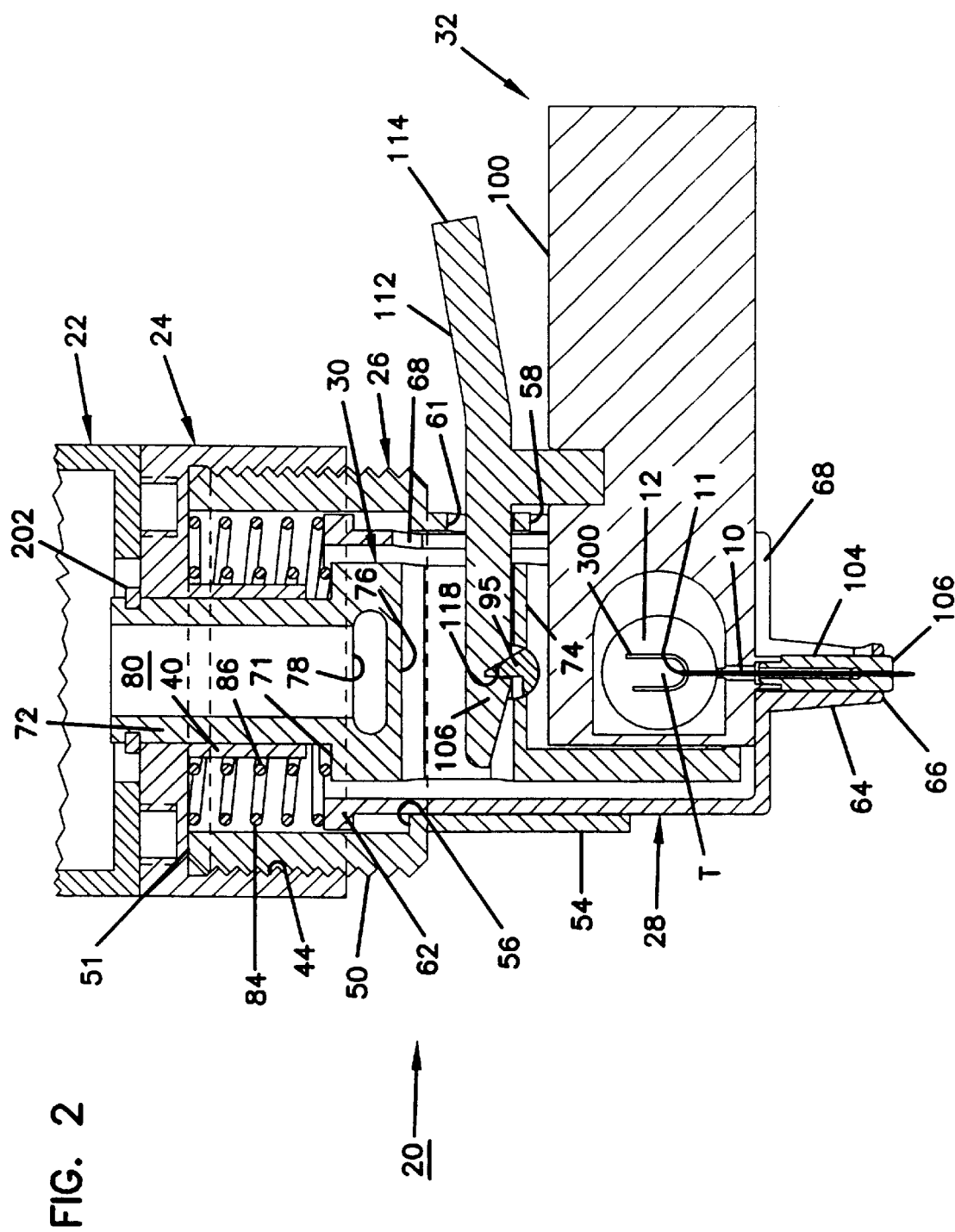
FIG. 2 is the view of FIG. 1 with the apparatus shown in an extended position.
Figure 3:
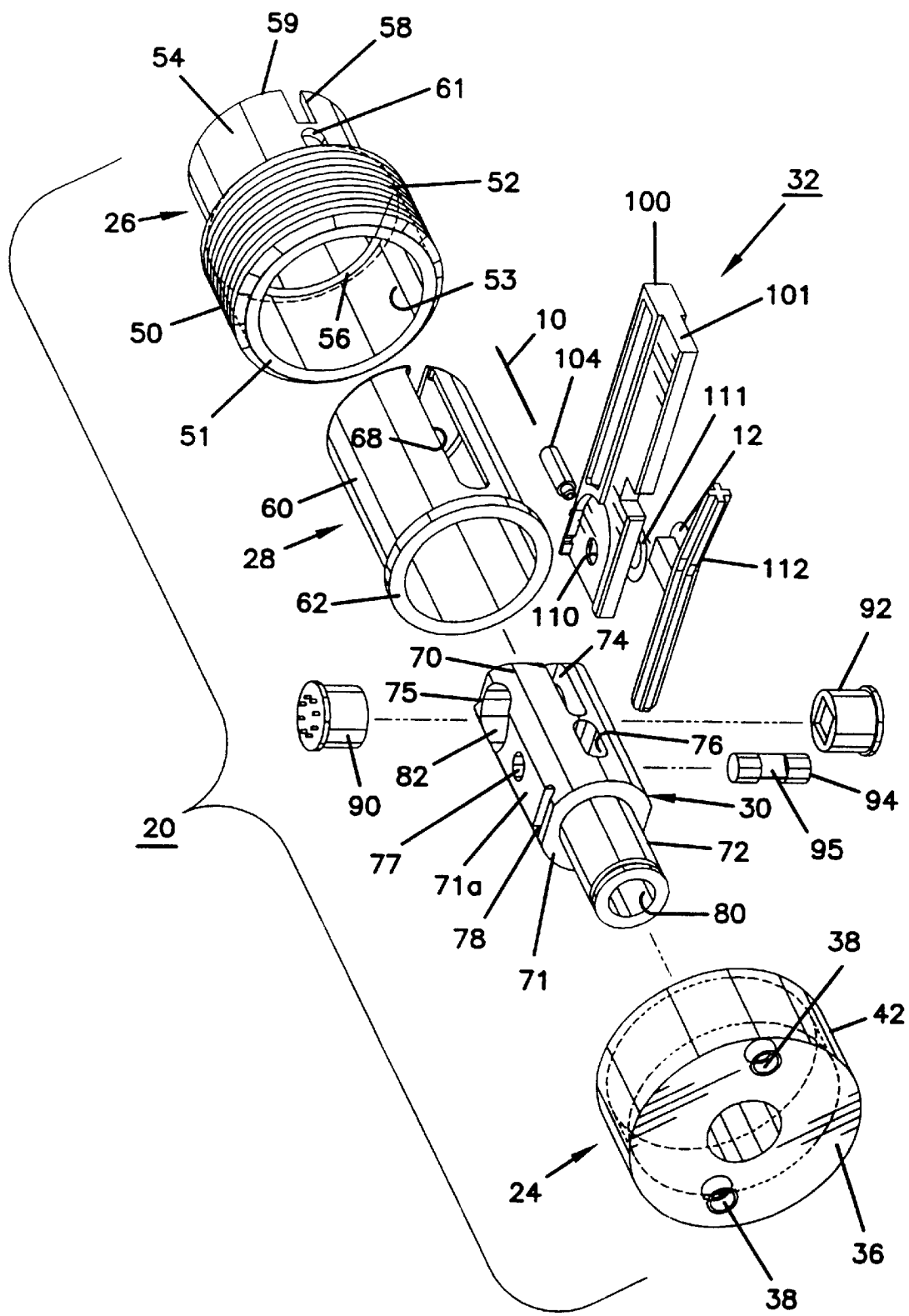
FIG. 3 is a perspective exploded view of the apparatus of FIG. 1.
Figure 4:
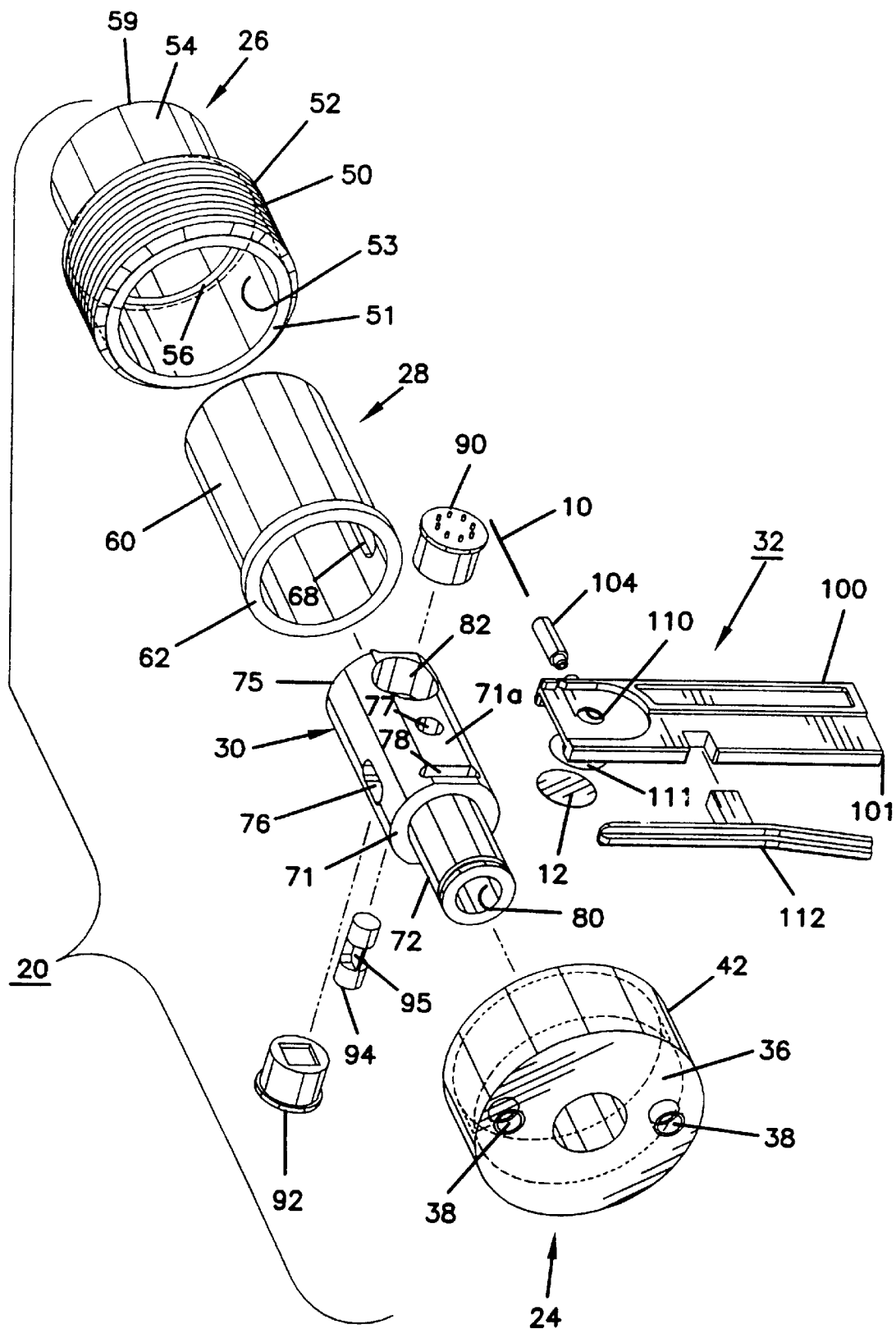
FIG. 4 is the view of FIG. 3 rotated 90° to the right of the view of FIG. 3.
Figure 5:
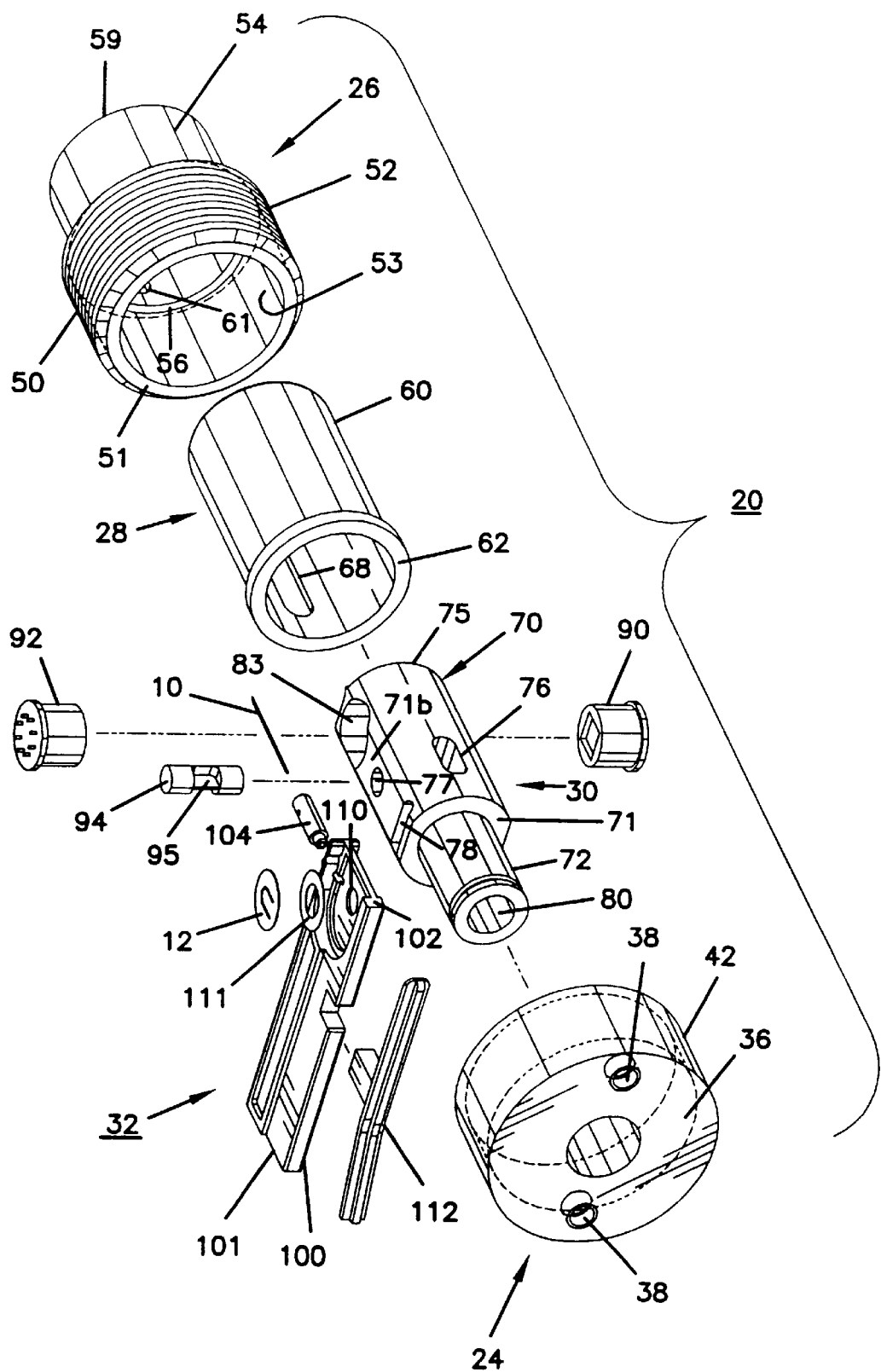
FIG. 5 is the view of FIG. 4 rotated 90° to the right of FIG. 4.
Figure 6:
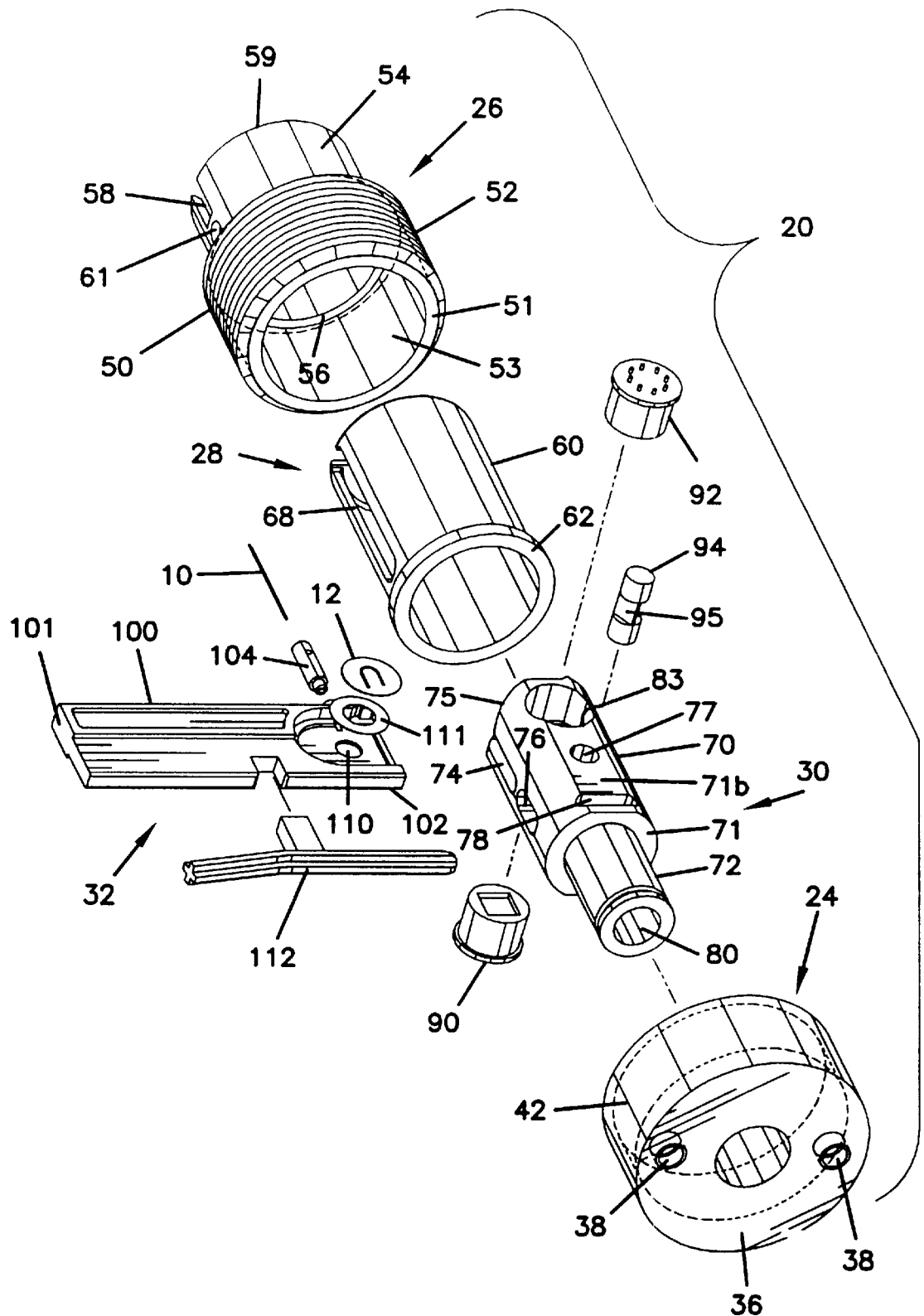
FIG. 6 is the view of FIG. 5 rotated 90° to the right of FIG. 5.

Main housing 22 is shown only in section in FIGS. 1 and 2. Main housing 22 is sized to be gripped by a patient such that the apparatus 20 may be urged against the patient's skin for purpose of collecting interstitial fluid as will be described. In addition to constituting a handle which can be grasped by the patient, the main housing 22 will contain electronics and the like for generating power for a light source as will be described and for analyzing signals from a light detector (as will be described) in order to calculate the level of constituents, such as blood glucose, contained within a sample of interstitial fluid. Such electronics are not shown but it will be appreciated that such electronics are well within the skill of the art. Examples of circuits for analyzing sampling light are described in commonly assigned U.S. Pat. No. 5,115,133 to Knudson dated May 19, 1992 and the aforementioned International Publication No. WO95/10223.

Figure 16:
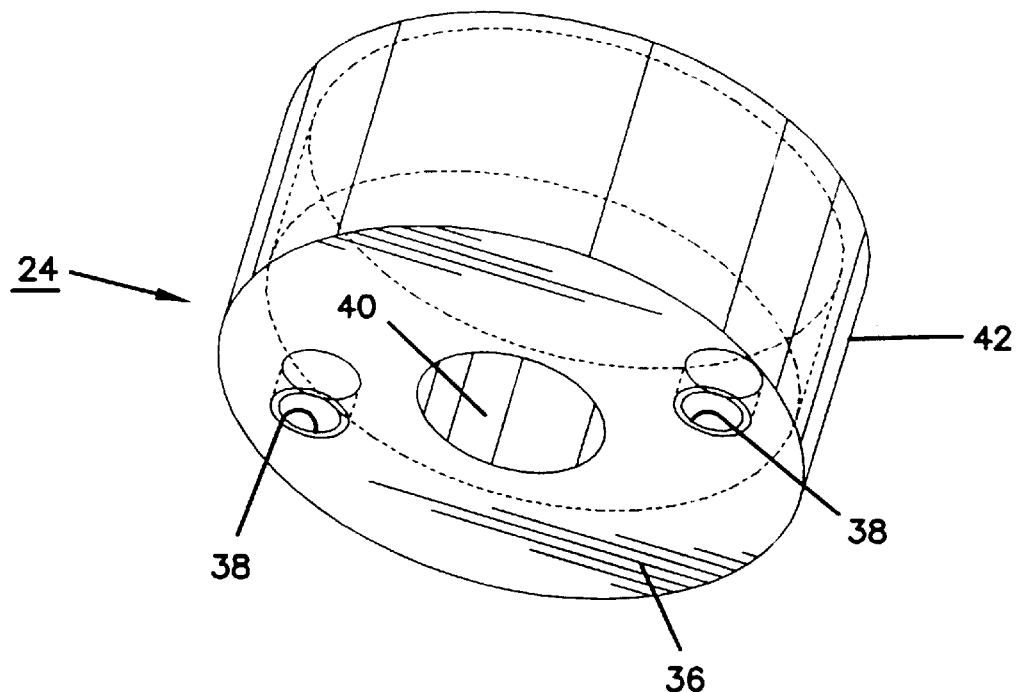
FIG. 16 is a perspective view of a base for use in the apparatus of FIG. 1.
Figure 17:
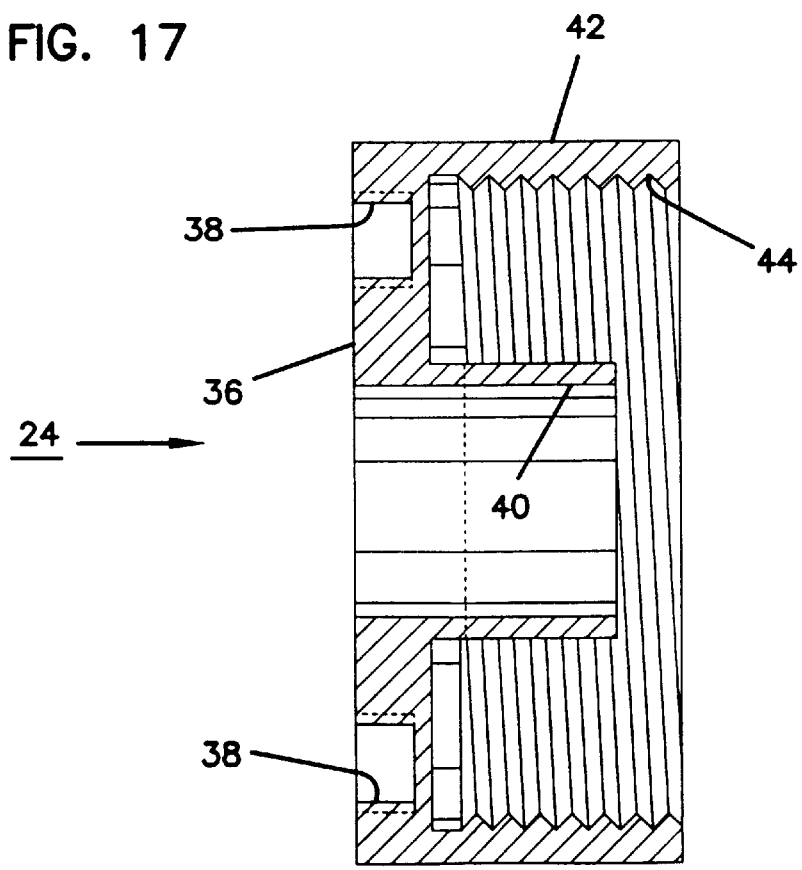
FIG. 17 is a sectional view of the base of FIG. 16.

The base 24 is separately shown in FIGS. 16 and 17. Base 24 is substantially cylindrical and is provided with an end plate 36 having holes 38 extending at least partially therethrough with the holes 38 sized to receive any suitable fastening means such as bolts or the like for fastening of the end plate 36 to the main housing 22. The base 24 further includes an inner hollow cylinder 40 extending from plate 36 with the inner cylinder 40 being coaxial with an outer cylinder 42 of the base 24. Outer cylinder 42 has a threaded inner surface 44.

Figure 14:
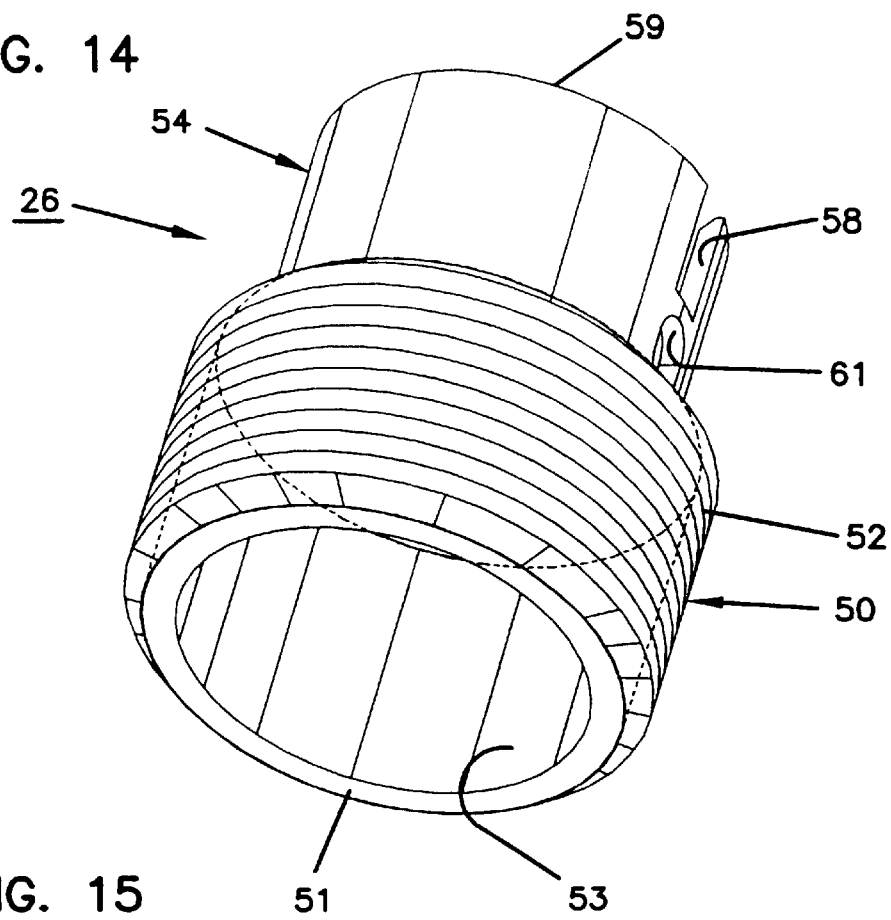
FIG. 14 is a perspective view of a collar for use in the apparatus of FIG. 1.
Figure 15:
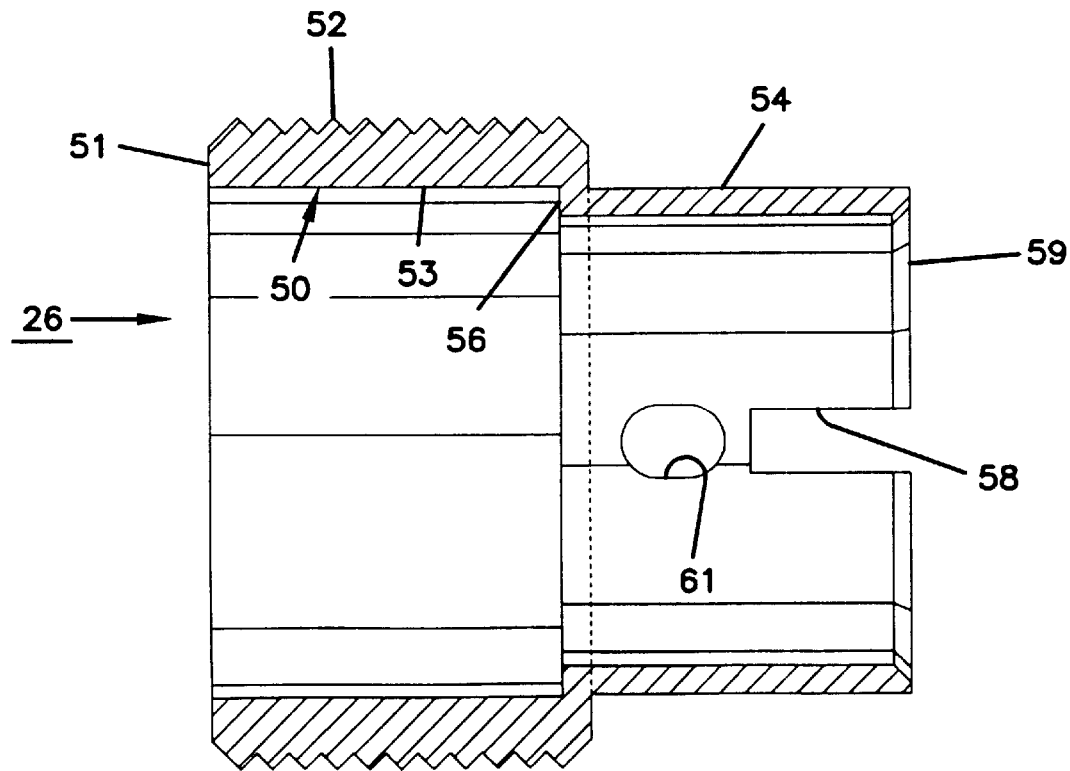
FIG. 15 is a sectional view of the collar of FIG. 14.

The collar 26 is separately shown in FIGS. 14 and 15. The collar 26 includes an enlarged cylindrical portion 50 sized to be received within base 24 and with an end 51 abutting the end plate 36 of base 24. An outer wall 52 is threaded to mate with the internal threading 44 of base 24. An inner wall 53 of cylindrical portion 50 remains spaced from inner cylinder 40 to define a void for receiving springs as will be described (and as shown in FIGS. 1–2). The collar 26 also includes a reduced diameter portion 54 with the reduced diameter portion 54 and the enlarged diameter portion 50 connected at an annular stop surface 56 shown in FIG. 15. For purposes that will become apparent, the reduced diameter portion 54 includes a slot 58 at an end 59 of portion 54. Linearly aligned with slot 58 is a hole 61.

Figure 12:
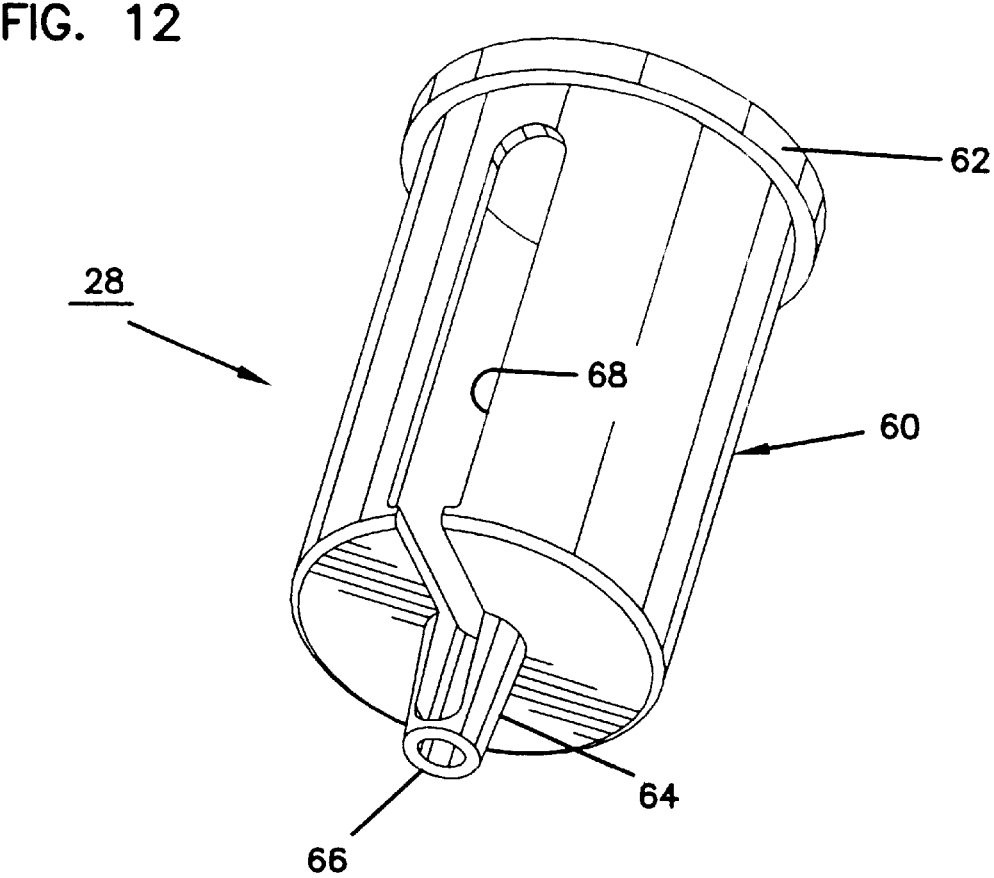
FIG. 12 is a perspective view of a shell for use in the apparatus of FIG. 1.
Figure 13:
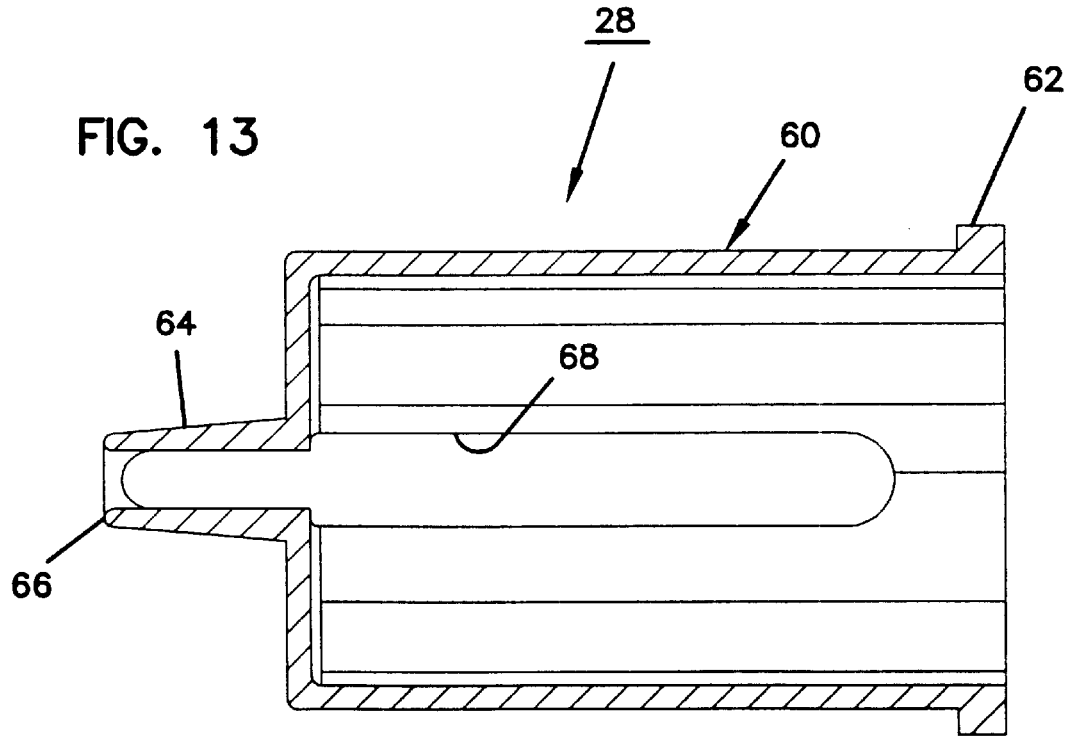
FIG. 13 is a sectional view of the shell of FIG. 12.

The shell 28 is separately shown in FIGS. 12 and 13. The shell 28 includes a cylindrical body 60 sized to be slidably received in close tolerance within the reduced diameter cylindrical portion 54 of collar 26. The cylindrical body 60 terminates at a flange 62 positioned to abut stop surface 56 of collar 26. Accordingly, the shell 28 is slidable within the collar 26 with the flange 62 movable between the stop surface 56 of collar 26 and the end plate 36 of base 24.

The cylindrical body 60 has at its end opposite flange 62 a reduced diameter portion 64 which is coaxial with the main cylindrical body 60. The reduced diameter portion 64 terminates at a first pressure ring 66 with the plane of the opening of the pressure ring 66 being generally perpendicular to the cylindrical axis of body 60. An elongated slot 68 extending generally in the direction of the axis of body 60 is provided extending through the shell 28 with the slot 68 extending substantially the length of the body 60 and substantially the length but not entirely through the sidewall of the reduced diameter portion 64 such that ring 66 is an uninterrupted ring. However, a segmented ring or other incomplete ring would be satisfactory.

The optics housing 30 is separately shown in FIGS. 7–11 and includes a generally cylindrical main body 70 (with flat side walls 71a, 71b) having extending axially therefrom a reduced diameter cylinder 72 (surrounded by surface 71) having an annular slot 73. The reduced diameter cylinder 72 is sized to be slidably received within the inner cylinder 40 of base 24 as best shown in FIGS. 1 and 2.

The main body 70 includes a first axial slot 74 extending partially through a distal end 75 of the body 70. Disposed axially spaced from slot 74 is a second slot 76 extending through the main body 70. A pin receiving hole 77 extends through body 70 perpendicular to slot 76. Ninety degrees offset from slots 74, 76 are access holes 78 in communication with a hollow interior 80 of cylinder 72. Ninety degrees offset from slot 74 are pockets 82, 83 with axes of the pockets 82, 83 in coaxial alignment with one another and in communication with the slot 74. The base end 75 has a ramped ridge 79 extending parallel to hole 77.

In the assembly, as best shown in FIGS. 1 and 2, a first biasing spring 84 is positioned to act between the base plate 36 of base 24 and the flange 62 of shell 28 urging the shell 28 away from the base plate 36. A second biasing spring 86 is positioned to act against the base plate 36 of base 24 and an engaging surface 71 on cylinder 70 thereby urging the optics housing 30 axially away from the base plate 36.

As shown in FIGS. 3–6, a light source 90 is contained within pocket 82. A light detector 92 is contained within pocket 83. Electrical leads (not shown) from both the light source 90 and light detector 92 may be passed between the opposing exterior surfaces 71a, 71b of cylinder 70 and the interior surface of shell cylinder 60 with the leads then passed through the holes 78, into hollow interior 80 of cylinder 72 and directed thus into the circuitry (not shown) contained within the housing 22. The light source 90 and light detector 92 are aligned to define a light path therebetween. The light source 90 generates a testing wavelength. The light detector 92 is selected to measure the intensity of wavelengths including the intensity of the testing wavelength.

Figure 26:
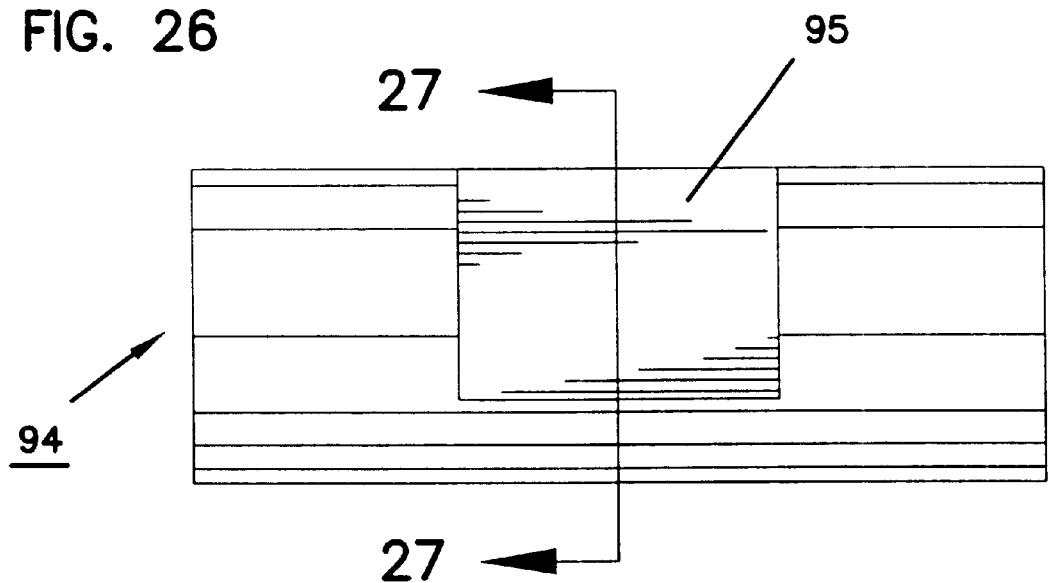
FIG. 26 is a side elevation view of a catch pin for the sampler of FIG. 18.
Figure 27:
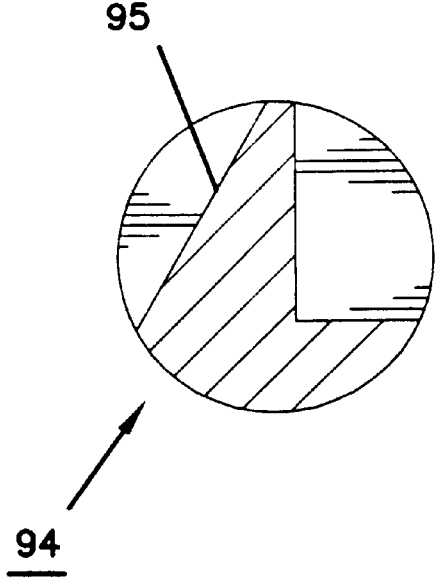
FIG. 27 is a view taken along line 27—27 in FIG. 26.

A lock pin 94 (shown separately in FIGS. 26–27) is contained within optics housing 30 in hole 77 with the lock pin 94 positioned at a 90° angle to the plane of the slot 74. The pin 94 has a ramp 95 disposed in slot 76. In the assembly shown in FIGS. 1–6, the slots 74, 76 of the optics housing 30 are in alignment with the slot 68 of the shell 28.

As shown in FIGS. 18–25, the sampler 32 includes a body 100 formed of injection molded plastic. The body 100 includes a rear handle portion 101 and a forward sampling portion 102. The handle portion 101 is sized to be gripped by the fingers of a user. At the sampling end 102, the body 100 is provided with a hub or piston 104. The piston 104 is cylindrical and sized to be received in close sliding tolerance within the reduced diameter cylinder 64 of shell 28. The piston terminates at a flat second pressure surface 106 which is generally perpendicular to the axis of the needle 10. While a flat surface 106 is preferred, other shapes (e.g., concave) could be used.

The needle 10 protrudes beyond the surface 106 a distance equal to a desired penetration of the needle 10 into a patient's skin layer. As disclosed in the aforementioned international publication, distance of protrusion of needle 10 is about 1.5 mm to ensure protrusion of the needle 10 into but not through a dermal layer of a patient's skin. At the sampling end 102, the main body 100 is provided with a relief 108 surrounding a hole 110 formed through the body. The hole 110 is in communication with a proximal end 11 of the needle 10. Accordingly, an absorbent material 12 such as the material 210' shown in FIGS. 16–20 of the aforementioned International Publication No. WO95/10223 may be placed within the relief 108 such that interstitial fluid which flows up the needle 10 will be deposited upon the membrane 12. The membrane 12 is held in place through any suitable means such as by an adhesive ring 111 (or, alternatively, ultrasonic bending or other bonding technique).

The hole 110 is positioned at a sampling location such that the hole 110 is in the light path between the light source 90 and the light detector 92 when the sampler 32 is placed within the apparatus 20 as will be described. The end 102 is sized to be received within the aligned slots 68, 74 of shell 28 and optics housing 30, respectively.

The main body 100 is provided with an arcuate rib 113 sized and shaped to abut an exterior surface of the optics housing 30 on both sides of the slot 74 and to curve beneath the base 75. A latching member 112 is connected to the body 100. The latching member 112 pivots at a point of connection to the body 100 and includes a lever arm 114 exposed at the handle portion 101 such that the lever member 114 may be depressed by a user. The latch 112 further includes a latching end 116 sized and positioned to be received within the hole 76 of the optics housing 30. The latching end 116 includes a detent 118 (FIGS. 1–2) positioned to engage and receive the ramp 95 of the lock pin 94 within the detent 118 when the sampler 32 is inserted within the slots 74, 76 in a predetermined alignment and with the sampling location 110 disposed within the light path between the source 90 and detector 92. A leading end of the locking end 116 is provided with a ramped surface to ride over the pin 94 upon insertion of the sampler 32 within the optics housing 30 and to provide a positive lock as the pin is received within the detent 118. To further secure the sampler 32 in optics housing 30 in the desired alignment, sampler housing 100 has a detent 117 (FIG. 23) to receive ridge 79 on the base 75 of optics housing 30. The sampler 32 may be easily removed by a user depressing end 114 thereby raising end 116 for the pin 94 to clear the detent 118 permitting removal of the sampler 32 from the apparatus.

With the construction thus described, a sampling end 102 may be placed within the aligned slots 74, 68. Over-insertion is avoided by reason of the sampling end 102 butting up against the interior of the optics housing 30. Further, the lock pin 94 received within the detent 118 and the ridge 79 in detent 117 ensure that the sampler 32 is not under-inserted into the slots 74, 76 by providing a user with a positive feedback indicating that the lock pin 94 has been received within the detent 118 indicating the sampler 32 is in the predetermined alignment. Accordingly, upon receipt of such feedback, the user is assured that the sampling location 110 is in alignment with the light path between the light source 90 and the light detector 92.

The first spring 84 urges the shell away from the base 24 such that the full length of the piston 104 and needle 10 may clear the first pressure ring 66 and be inserted through the slot 68 as the sampler 32 is loaded into apparatus 20.

Due to the locking at detents 118 and 117, sampler 32 is held in a predetermined alignment with the membrane 12 in the light path between light source 90 and light detector 92. To facilitate placement of sampler 32 within apparatus 20, the sampler 32 and apparatus 20 have mating external geometries. Namely, in the rest position of FIG. 1, the shell 28 is fully extended from base 36 by spring 86. Slot 58 of collar 26, slot 68 of shell 28 and slot 74 of optics housing 30 are aligned to permit insertion of end 102 of sampler 32. Further, in this position, slot 68 is sized so that needle 10 may pass ring 66 without interference. Also, in this position, slot 61 of collar 26, slot 68 of shell 28 and hole 76 of optics housing 30 are aligned to receive end 116 of lever arm 112.

Upon insertion, the mating geometry of sampler 32 and optics housing 30 insure the membrane 12 is accurately positioned. The ribs 113 acting against the external surface of optics housing 30 together with ribs 95, 79 received within detents 118, 117 securely couple the sampler 32 to optics housing 30 in accurate alignment and with the sampler 32 movable with the optics housing 30. As the optics housing 30 moves relative to shell 28 and collar 26, the sizing of slots 58, 61 and 68 avoid interference with movement of the sampler 32.

Upon initial placement of the apparatus against a patient's skin 200 (FIG. 28), the ring 66 first contacts a patient's skin 200 with the needle 10 being recessed behind the ring 66. Upon urging of the apparatus 20 against the skin 200, the ring 66 moves relative to the needle 10 against the bias of the first spring 84. Upon achieving such relative movement, the needle 10 then penetrates the skin 200 with the second pressure surface 106 of the piston 104 engaging the skin and with both springs 84, 86 resisting further penetration until both springs are engaged. Second spring 86 ensures a constant force acts on piston 106.

FIGS. 28–30 show a sequence of operation of the present apparatus. As shown in FIG. 28, during the rest state, the needle 10 is recessed behind the first pressure ring 66 to prevent damage to the needle 10 and inadvertent skin penetration. Upon initial urging of the pressure ring 66 against the skin (FIG. 29), the pressure ring 66 depresses the skin 200 and makes the skin taut in the area defined by the ring 66. Further, this urging of the pressure ring creates a pressurized area in the zone of the skin layer 200 directly beneath the ring 66. This is desirable since interstitial fluid beneath the skin 200 is believed to exist at a negative pressure. Creating a pressurized zone beneath the ring 66 is believed to assist in rapid collection of interstitial fluid within the needle 10. During this initial pressurization of the skin 200, the ring 66 moves relative to piston 104 until the needle 10 penetrates the skin 200 and the end 106 of the piston 104 abuts the skin 200 (FIG. 30). Further depression (which can occur against soft skin but which might not occur against more rigid skin) is shown in FIG. 31 where the piston end surface 106 protrudes slightly beyond the ring 66 to further increase the pressure acting in the collection zone of the skin 200 and with full penetration of the needle 10.

It has been found that this sequence of action significantly increases the rate at which interstitial fluid is collected through the needle 10 and deposited on the membrane 12 within the sampler 32.

After full penetration of the needle 10, internal circuitry may then be actuated to operate the light source 92. Absorption of the testing light through the collected sample provides an indication of the amount of the constituent contained on the sample.

In a preferred embodiment, springs 84, 86 are preloaded. Namely, in the rest position of FIGS. 1 and 28, first spring 84 exerts an urging force on shell 28 of about three pounds and with a spring constant of about four pounds per inch. Spring 86 is pre-loaded to about one pound and has a spring constant of about two pounds per inch. To accommodate the pre-loading of springs 84, 86, optics housing 30 is provided with a retaining ring 202 (shown only in FIGS. 1 and 2) in slot 73. The pre-loading of spring 84 insures a minimum skin pressure by ring 66 before penetration of the skin 200 by needle 10.

Figure 18:
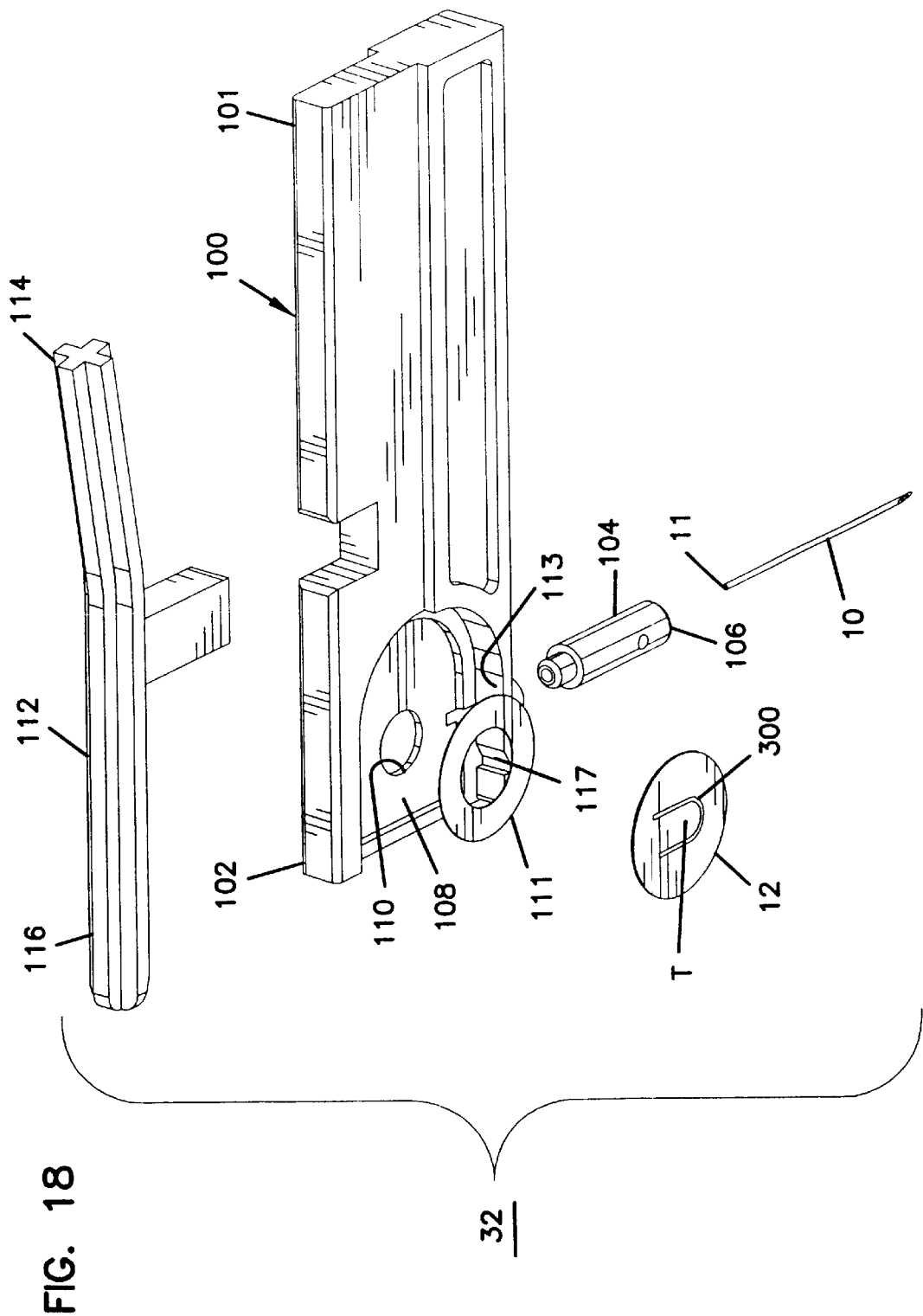
FIG. 18 is a top, left side and rear end exploded perspective view of a sampler for use in the apparatus of FIG. 1.
Figure 19:
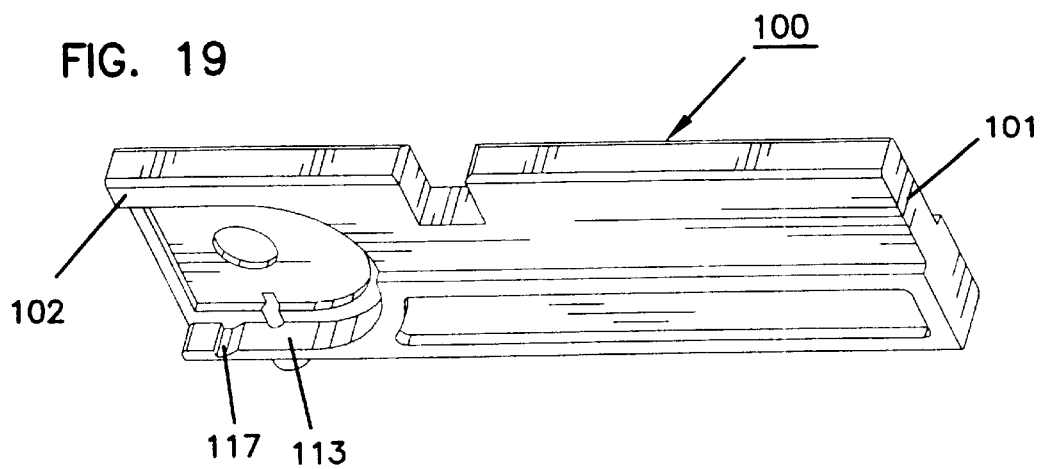
FIG. 19 is a top, left side and rear end perspective view of a sampler main body for the sampler of FIG. 18.
Figure 20:
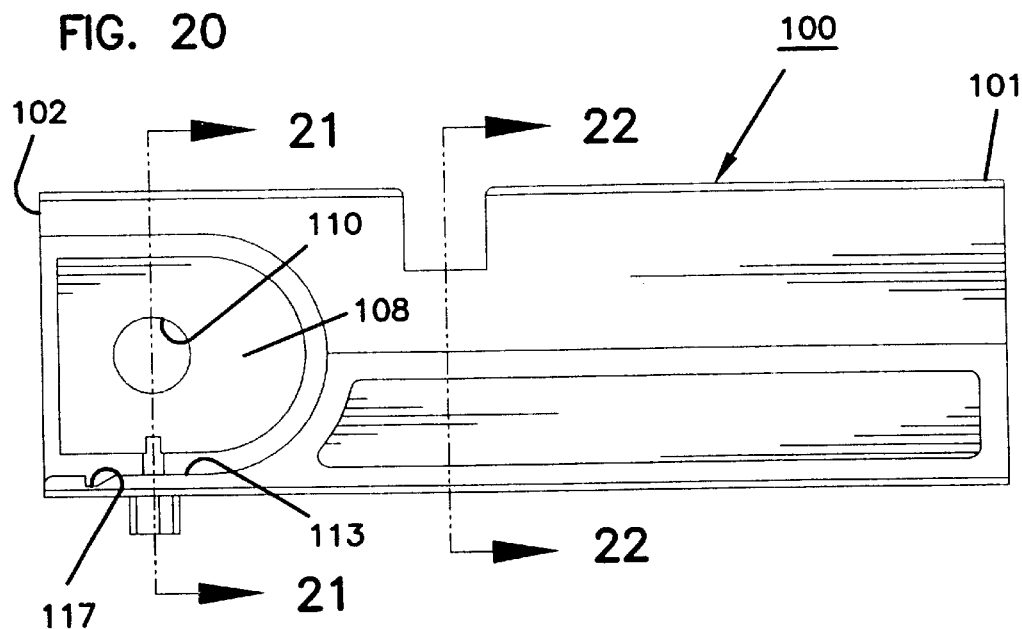
FIG. 20 is a left side elevation view of the sampler main body of FIG. 18 (with the opposite side being substantially identical)
Figure 21:
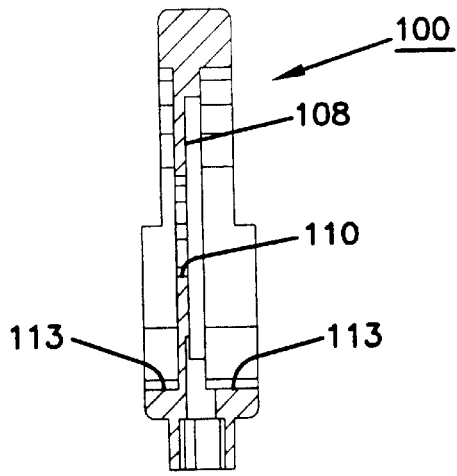
FIG. 21 is a view taken along line 21—21 of FIG. 20.
Figure 22:
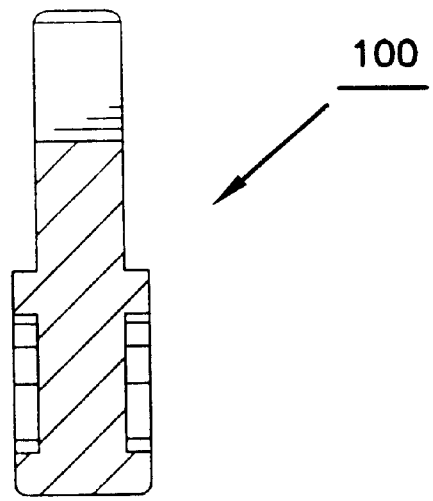
FIG. 22 is a view taken along line 22—22 of FIG. 20.
Figure 23:
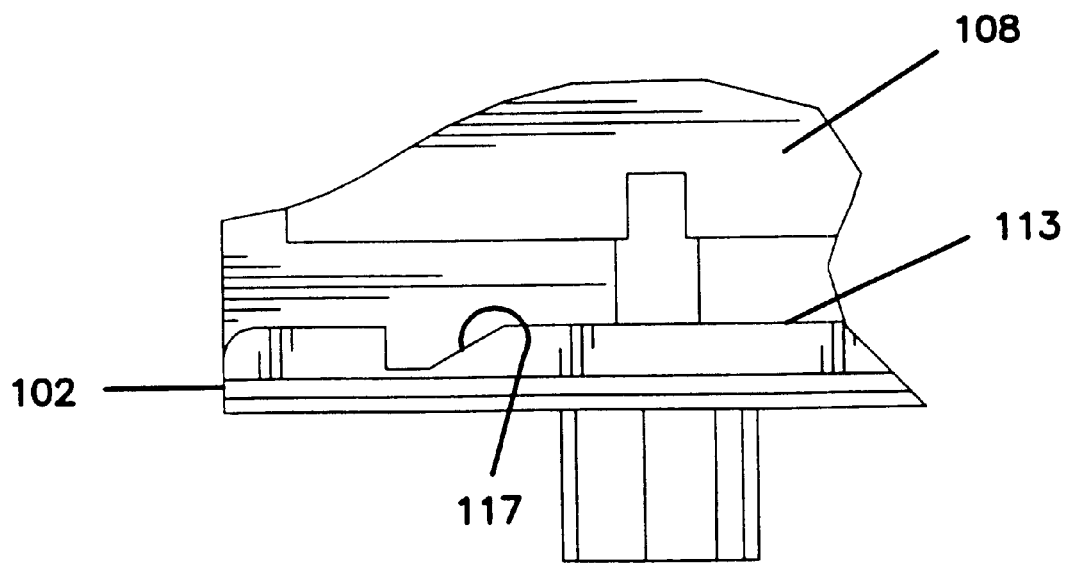
FIG. 23 is an enlarged bottom view of a front portion of the main body of FIG. 20.
Figure 24:
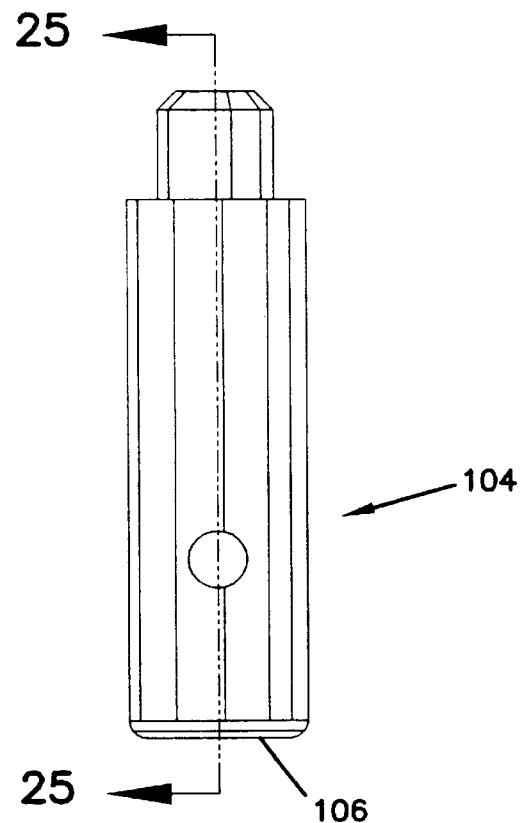
FIG. 24 is a side elevation view of a piston for the sampler of FIG. 18.
Figure 25:
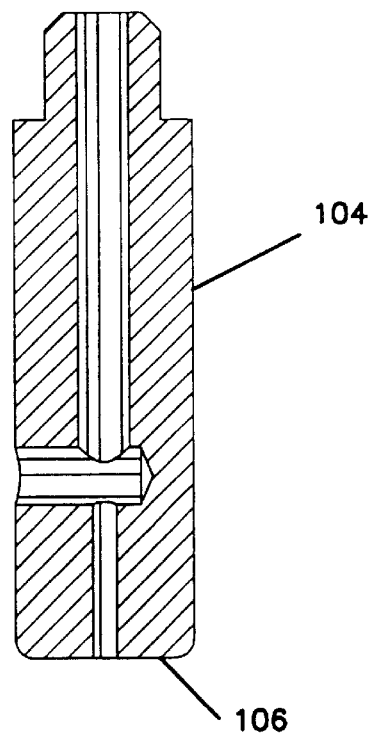
FIG. 25 is a view taken along line 25—25 in FIG. 24.

As shown best in FIGS. 1, 2 and 18, membrane 12 is provided with a U-shaped boundary 300. Boundary 300 is formed by ultrasonically or pressure treating membrane 12 to create a material density in boundary 300 which is greater than a material density of the remainder of the membrane 12. Therefore, boundary 300 provides an increased resistance to liquid flow compared to the remainder of the absorbent membrane 12. The end 11 of needle 10 is positioned to deposit interstitial fluid onto the interior of the U-shaped boundary 300. The increased density of the boundary 300 permits the fluid to flow within the interior of the boundary 300 but restricts fluid flow beyond the boundary 300. The target location ("T") of light through membrane 12 during testing is positioned within the boundary 300. Boundary 300 thus insures that a sufficient volume of collected fluid is in residence at the target location T during testing.

It will be appreciated that through use of the present invention the rate at which interstitial fluid is collected through the needle 10 is greatly enhanced over that shown in the aforementioned International Publication No. WO95/10223. Further, the sampling apparatus is contained within a low-cost sampler 32 which can be readily disposed after each use. The mating geometry of the sampler 32 with the internal geometry of the apparatus 20 ensures that the sampler 32 is placed within the apparatus 20 in a predetermined alignment with the sampling location in the light path between the source 90 and the detector 92. The sampling apparatus also ensures a proper positive locking position which may be released easily by an operator and the entire operation of insertion of the sampler within the apparatus and removal of the sampler for subsequent disposal is easily accomplished for a patient.

Having disclosed the present invention and a preferred embodiment, it will be appreciated that modifications and equivalents of the disclosed concepts may readily occur to one skilled in the art. It is intended that such modifications and equivalents shall be included within the scope of the claims which are appended hereto.

What is claimed is:

1. A method of collecting a sample of body fluid from a skin layer the method comprising:
   providing a sampling tool comprising a needle and a skin stretching member having opposing surfaces at least partially surrounding said needle, wherein said needle and said skin stretching member are independently movable relative to one another along a path substantially parallel to an axis of said needle;
   placing said skin stretching member against the skin of a patient with said opposing surfaces at least partially surrounding and defining a fluid collection area;
   advancing said skin stretching member relative to said needle to stretch a skin layer in the fluid collection area;
   advancing said needle relative to said skin stretching member thereby inserting said needle into the fluid collection area of the stretched skin layer; and
   collecting said sample of body fluid including interstitial fluid.

2. The method of claim 1 wherein said skin stretching member is circular.

3. The method of claim 2 further comprising causing body fluid to flow into the fluid collection area.

4. The method of claim 1 wherein said skin stretching member comprises a pressure ring.

5. The method of claim 1 further comprising placing an absorbent membrane in fluid communication with said needle wherein said collected body fluid is deposited on said absorbent membrane.

6. The method of claim 5 further comprising testing said body fluid deposited on said absorbent membrane with light.

7. The method of claim 1 further comprising testing said collected body fluid for determining the concentration of at least one constituent.

8. The method of claim 1 wherein said advancing said skin stretching member comprises employing a first spring and said advancing said needle comprises employing a second spring.

9. A method of collecting a sample of body fluid from skin, the method comprising:

providing a fluid collection device comprising a piston having a distal surface, a needle operatively connected to said piston and having a distal end extending a distance from said distal piston surface, and a pressure surface adjacent said needle, said piston and said pressure surface being independently movable relative to one another along a path substantially parallel to the axis of said needle;

placing said pressure surface against the skin of a patient to define a fluid collection area advancing said pressure surface relative to said piston thereby stretching skin within the fluid collection area;

advancing said piston relative to said pressure surface thereby inserting said needle into the fluid collection area of the skin; and collecting body fluid.

10. The method of claim 9 wherein stretching the skin comprises drawing tight the skin.

11. The method of claim 9 further comprising further advancing said piston relative to said pressure surface wherein said distal piston surface extends distally beyond said pressure surface.

12. The method of claim 9 further comprising testing said collected body fluid for determining the concentration of at least one constituent.

13. The method of claim 9 wherein said advancing said pressure surface comprises employing a first spring and said advancing said piston comprises employing a second spring.

* * * * *